United States Patent
Dyszlewski et al.

(10) Patent No.: US 6,926,883 B1
(45) Date of Patent: *Aug. 9, 2005

(54) GROUP (VII) TRANSITION-METAL COMPLEXES WITH MULTIDENTATE AMINOPOLYCARBOXYLATE LIGANDS AND A KIT FOR PRODUCING THEM

(75) Inventors: Mary M. Dyszlewski, Creve Coeur, MO (US); Roger Alberto, Winterthur (CH); Joseph E. Bugaj, St. Charles, MO (US)

(73) Assignee: Mallinckrodt Inc, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/030,741
(22) PCT Filed: Jun. 28, 2000
(86) PCT No.: PCT/US00/17813
§ 371 (c)(1), (2), (4) Date: Nov. 30, 2001
(87) PCT Pub. No.: WO01/00637
PCT Pub. Date: Jan. 4, 2001

Related U.S. Application Data
(60) Provisional application No. 60/140,989, filed on Jun. 29, 1999.

(51) Int. Cl.$^7$ .............................. A61K 49/00; C07F 5/00
(52) U.S. Cl. ..................... 424/1.65; 424/1.11; 424/9.36; 534/10; 534/14
(58) Field of Search ..................... 534/10–16; 424/1.11, 424/1.65, 9.3, 9.36, 9.1; 206/223, 569, 570

(56) References Cited

U.S. PATENT DOCUMENTS 6,344,178 B1 * 2/2002 Alberto et al. ............. 424/1.65
6,359,119 B1 * 3/2002 Pipes et al. ................... 534/14

FOREIGN PATENT DOCUMENTS

EP      1013642 A2  *  6/2000
WO      WO98-48848  *  11/1998

OTHER PUBLICATIONS

Alberto et al (1995), Journal of Organometallic Chemistry, 493, pp. 119–127.*

Alberto et al (1998), J. Am. Chem. Soc, 120, ppl. 7987–7988.*

* cited by examiner

Primary Examiner—Dameron L. Jones (57) ABSTRACT

The invention relates to novel aminocarboxylate ligands that are suitable for complexing with a radionuclide, and are useful as imaging agents for diagnostic purposes. In accordance with the present invention, a method of preparing a compound of formula (I): fac-$[M(CO)_3(OH_2)_3]^+$, wherein M is Mn, $^{99m}$Tc, $^{186}$Re or $^{188}$Re, involves reacting a metal in permetallate form with carbon monoxide and a reducing agent, wherein a mixture of a basic borate buffer and a reducing agent soluble in water but not substantially decomposed by water is solved in a water containing solvent system containing a solution of the metal in permanganate, pertechnetate or perrhenate form in the presence of carbon monoxide. The compound of formula (I) can be reacted with a ligand $L_x$ to form a compound of formula (II): fac-$[M(CO)_3(X)_2L_1]^n$, wherein M is as defined above $L_x$ is a multidentate ligand, and n is a charge of the ligand $L_x$ increased with one + charge. The invention also is directed to novel compounds, and kits for carrying out the disclosed methods.

13 Claims, 5 Drawing Sheets

GROUP (VII) TRANSITION-METAL COMPLEXES WITH MULTIDENTATE AMINOPOLYCARBOXYLATE LIGANDS AND A KIT FOR PRODUCING THEM

APPLICATION CROSS-REFERENCE

This application is a national phase application under 35 U.S.C. Section 371 of International Application PCT/US00/17813 filed Jun. 28, 2000, which claims benefit of U.S. Provisional Patent Application No. 60/140,989 filed Jun. 29, 1999.

FIELD OF THE INVENTION

The present invention relates to novel ligands for forming radionuclide complexes, new complexes incorporating such ligands, processes for preparing such complexes, imaging agents incorporating such complexes, and methods of imaging using such imaging agents.

BACKGROUND OF THE INVENTION

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which upon introduction to a biological subject, becomes localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent designed to target the specific organ or tissue site, various auxiliary agents which affix the radionuclide to the carrier, water or other delivery vehicles suitable for injection into, or aspiration by, the patient, such as physiological buffers, salts, and the like. The carrier agent attaches or complexes the radionuclide to the carrier agent, which results in localizing the radionuclide being deposited in the location where the carrier agent concentrates in the biological subject.

Technetium-99m ($^{99m}$Tc) is a radionuclide which is widely known for its uses in tissue imaging agents. Due to its safety and ideal imaging properties, this radionuclide is conveniently available commercially in the oxidized pertechnetate form ($^{99m}$TcO$_4^-$) hereinafter "pertechnetate-Tc99m". However, pertechnetate will not complex with the most commonly used biological carriers for radionuclide tissue imaging. Thus, technetium-labelled imaging agents are generally prepared by admixing a pertechnetate-Tc99m isotonic saline solution, a technetium reductant (reducing agent) such as stannous chloride or sodium dithionite, and a chelate conjugated to the desired peptide carrier agent for targeting the organ of interest. Alternatively, an intermediate transfer liquid-technetium 99m complex may be prepared prior to addition to the chelate-biological molecule to maintain the oxidation state within a desired level. Examples of such include 99m Tc-tartrate or 99m Tc-gluconate.

Another problem is that technetium-containing scintigraphic imaging agents are known to be unstable in the presence of oxygen, primarily since oxidation of the reductant and/or the technetium –99m destroys the reduced technetium –99m/targeting carrier complex. Accordingly, such imaging agents are generally made oxygen-free by saturating the compositions with oxygen-free nitrogen gas or by preparing the agents in an oxygen-free atmosphere. Stabilization of imaging agents can also be achieved through chemical means. U.S. Pat. No. 4,232,000, Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980 discloses the use of gentisic acid as a stabilizer.

In published PCT Application No. PCT/US98/07979 (International Publication No. WO 98/48848), which is incorporated herein in its entirety by reference, a method was disclosed for preparing a compound of the general formula (I): fac[M(CO)$_3$(OH$_2$)$_3$]$^+$ wherein M is Mn, $^{99m}$Tc, $^{186}$Re or $^{188}$Re, by reacting a metal in the permetallate form with carbon monoxide and a reducing agent, characterized in that a mixture of a base, a reducing agent soluble in water but not substantially decomposed by water, and optionally a stabilizing agent is solved in a water containing solvent system containing a solution of the metal in the permanganate, pertechnetate or perrhenate form in the presence of carbon monoxide and optionally in the presence of a halide. The ligands disclosed for labeling biologically active molecules have a tendency to stabilize metals in their low oxidation states. These ligands have in common the presence of low-lying vacant orbitals of the correct symmetry to form pi-bonds by accepting electrons from filled metal d-orbitals, a phenomenon known as backbonding. The ligands indicated in the patent application include isonitriles, phosphines, thioethers, Schiff bases, and pyridine-, imidazole-, and pyrazole-type groups. In particular, the amino acid histidine is indicated as an ideal chelate. For some purposes a problem with using histidine and other unsaturated organic molecules as chelates is that the resulting labeled compound is highly lipophilic resulting in high liver and blood uptake. The predominant hepatobiliary uptake and clearance are for some purposes undesirable characteristics for the targeted imaging agents.

The publications and other materials used herein to illuminate the background of the invention or provide additional details respecting the practice, are incorporated by reference, and for convenience are respectively grouped in the appended List of References.

SUMMARY OF THE INVENTION

In accordance with the present invention, a method of preparing a compound of formula $$\text{fac-[M(CO)}_3\text{(OH}_2\text{)}_3]^+ \tag{I}$$

wherein M is Mn, $^{99m}$Tc, $^{186}$Re or $^{188}$Re,
involves reacting a metal in permetallate form with carbon monoxide and a reducing agent, wherein a mixture of a basic borate buffer and a reducing agent soluble in water but not substantially decomposed by water is solved in a water containing solvent system containing a solution of the metal in permanganate, pertechnetate or perrhenate form in the presence of carbon monoxide. The compound of formula (I) can be reacted with a ligand $L_x$ to form a compound of the formula $$\text{fac-}[M(CO)_3(X)_2L_1]^n \quad\quad (II)$$

wherein M is as defined above, $L_x$ is a multidenate ligand, and n is a charge of the ligand $L_x$ increased with one + charge. The invention also is directed to novel compounds, and kits for carrying out the disclosed methods.

DETAILED DESCRIPTION OF THE INVENTION

The present invention relates to the use of multidentate ligands, which preferably are aminopolycarboxylate chelates for labeling biological molecules which generally result in more hydrophilic compounds that are predominantly excreted through the kidneys. Although these types of ligands are not pi-acids and generally do not stabilize technetium in a low oxidation state, they do form very stable complexes with the Tc(I) tricarbonyl precursor and have favorable biodistribution characteristics. In particularly preferred embodiments, the ligands for use in accordance with the present invention are not bidentate. Examples of aminopolycarboxylate ligands include diethylenetriaminepentaacetic acid (DTPA), ethylenediaminetetraacetic acid (EDTA), and 1,4,7,10-tetraazacyclododecane-1,4,7,10-tetraacetic acid (DOTA). Preferred aminopolycarboxylate chelates are those which contain one tridentate face which can attach to the technetium center, such as iminodiacetic acid (IDA), nitrilotriacetic acid (NTA), and triazacyclononanetriacetate.

Methods are disclosed for preparation of facial metal tricarbonyl compounds and further co-ordinated facial metal tricarbonyl compounds. The invention further relates to the use of said facial metal tricarbonyl compounds in the labeling of biologically active substrates and other ligands, and to a kit for preparing a facial metal tricarbonyl compound or further co-ordinated facial metal tricarbonyl compounds.

The application of metal complexes, with a wide variety of radionuclides, in the field of nuclear medicine has become a major tool in diagnosis and also more recently in therapy. The metal complexes are often attached to a biologically active substrate that acts as a targeting agent. One of the most widely applied procedures for the metal-labeling of biologically active substrates such as proteins, peptides, sugars or small biologically active compounds consists in stabilizing the M(V)=O moiety of (radioactive) metals of group 7B of the periodic table with different tetradentate ligands. After reduction, the M(V)=O moiety is intermediately stabilized with a larger amount of an auxiliary ligand such as glucoheptonate which is subsequently substituted by the chelator attached to the system to be labeled. This method has proven to be successful in many cases but suffers from some major disadvantages such as the required high denticity and the bulkiness of the ligand and the difficulty in synthesizing and attaching such ligand.

It is known in the art (Alberto et al., 1994a) that facial metal tricarbonyl complexes of radioactive metals of group 7B of the periodic table are very convenient starting materials for substitution reactions in organic solvents as well as in water, as these compounds are stable in water for weeks, even if exposed to air. Therefore said compounds would be very useful for the labeling of biologically active substrates, such as amino acids, peptides, proteins, sugars and any receptor binding molecules. A major drawback, however, of these compounds until now is that they have only been available from high temperature carbonylation reactions and with the aid of the pyrophoric and toxic and therefore dangerous reducing agent $BH_3$ (Alberto et al., 1994a).

It is the objective of the present invention to provide for a method of preparing facial metal tricarbonyl compounds of (radioactive) metals of group 7B with the aid of easily available and low-toxic starting materials at moderate temperature and at normal pressure of CO, in a reasonable time and with high yield.

Such a method would be a powerful tool that can be used for the synthesis of diagnostic and therapeutic agents, especially for the synthesis of said diagnostic and therapeutic agents derived from radioactive metals with a short lifetime, in order to have access to these labeled compounds in poorly-equipped hospital laboratories. When the above mentioned diagnostic agent is labeled with a radionuclide it can be detected by the so-called single photon emission computerized tomography (SPECT and SPET), when it is labeled with a paramagnetic metal atom it can be detected by magnetic resonance imaging.

The above-defined objective can be achieved, according to the present invention, by a method of preparing a compound of the general formula $$\text{fac-}[M(CO)_3(OH_2)_3]^+ \quad\quad (I)$$

wherein M is Mn, $^{99m}$Tc, $^{186}$Re or $^{188}$Re, by reacting a metal in the permetallate form ($MO_4^-$ form) with carbon monoxide and a reducing agent, characterized in that a mixture of a base, a reducing agent soluble in water but not substantially decomposed by water, and optionally a stabilizing agent is solved in a water containing solvent system containing a solution of the metal in the permanganate, pertechnetate or perrhenate form in the presence of carbon monoxide.

The metal M is preferably $^{99m}$Tc, $^{186}$Re or $^{188}$Re, as these radionuclides, when used in diagnostic or therapeutic agents, have the advantage that they can be applied in very low concentrations, which minimizes the risk of toxicity.

The term "not substantially decomposed by water" means that upon the addition of the solution of permanganate, pertechnetate or perrhenate in water, the velocity of the decomposition reaction of the reducing agent with water is zero or very low compared with the reaction of said reducing agent with the permanganate, pertechnetate or perrhenate, so that the reaction with said permetallate is completed when still enough of the reducing agent is present.

It is very surprising that a quantitative reduction of permetallates in water containing solvent systems can be achieved at moderate temperature and in reasonable times with reducing agents that are nucleophilic and that are generally considered as less reactive than the electrophilic reducing agent BH$_3$ known in the art.

The method of the invention can be easily performed just by mixing the permetallate solution with the other reagents in the presence of carbon monoxide. The permetallate solution may optionally contain halide ions needed for the elution of the permetallate from a generator. The carbon monoxide may be supplied by using a closed system with an atmosphere containing a sufficient amount of carbon monoxide, or by flushing the carbon monoxide gas through the solution. Preferably the gas is substantially pure carbon monoxide.

The base used is preferably a basic borate buffer. Other bases include inorganic bases, selected from the group of stable hydroxides and carbonate salts such as NaOH, KOH, NaHCO$_3$, NaCO$_3$, KHCO$_3$, K$_2$CO$_3$, Ca(OH)$_2$ and Mg(OH)$_2$. The base is added in a molar ratio to the reducing agent of between 0.1 and 2, and preferably in a molar ratio of approximately 0.35.

The reaction can be performed with and without a stabilizing agent. As a stabilizing agent gentisate (2,5-dihydroxybenzoate), glucoheptonate, citrate or tartrate can be used, e.g. as NaK-tartrate. The stabilizing agent is added to the reaction mixture in such an amount that its concentration is higher than that of the metal to be reduced.

In preferred embodiments, the mixture includes L-tartaric acid.

In particularly preferred embodiments, the mixture includes lactose.

For the reduction several reducing agents can be used, such as borohydride anion (BH$_4^-$) or substituted borohydride anion wherein up to three of the hydrogen atoms which comprise the borohydride anion have been independently replaced by inert substituents. Examples of said inert substituents are alkoxy or alkylcarbonyloxy groups containing 1 to 10 carbon atoms and cyano groups. The counterion of the reducing group may consist of a metal of group 1A or 2A of the periodic table or zinc or an ammonium or tetrasubstituted ammonium or tetrasubstituted phosphonium ion, wherein the four substituents are each independently alkyl groups containing from 1 to 10 carbon atoms, hydroxyalkyl groups or alkoxyalkyl groups containing from 2 to 10 carbon atoms or aryl groups.

Preferred reduction reagent is borohydride anion, especially in the form of compounds such as sodium borohydride, potassium borohydride, lithium borohydride and zinc borohydride. The most preferred reducing agent is KBH$_4$.

The reducing agent is reacted with the permetallate in a molar ratio higher than 3. The reduction reaction can be performed at a temperature between 20° C. and 100° C. The preferred reaction temperature is approximately 75° C. The heating of the reaction mixture can be performed in the normal way but also by microwave heating. The reaction can also be performed by the application of the ultrasound, e.g. by carrying out the reactions in an ultrasonic bath at room temperature, normally leading to the same reaction rate at lower reaction temperature.

The compound of the general formula (I) obtained is very suitable for the labeling of biologically active substrates, such as amino acids, peptides, proteins, sugars, small receptor binding molecules or cells.

Examples of peptides that may be labeled are growth factors, somatostatin, bombesin, insulin, LHRH, gastrin, gastrin releasing peptide, thyrotropin releasing hormone, thyroid stimulating hormone, prolactin, vasoactive intestinal peptide (VIP), pituitary adenylate cyclase-activating polypeptide (PACAP), angiotensin, neurotensin, interferons, IL-1, IL-4 and IL-6, monoclonal antibodies and their analogues and derivative. After labeling with a suitable labeling substance these peptides can e.g. be used in the detection and localization of treatment of malignant human tumors.

Examples of sugars that may be labeled are glucose and deoxyglucose and derivatives of said compounds.

Small receptor binding molecules are defined as non-peptide molecules which are binding to a receptor and normally have a molecular mass below approximately 500 Daltons.

Examples of small receptor binding molecules that may be labeled are substances for the serotonergic system as described in WO 96/30054, or substances for the dopaminergic system (e.g. raclopride, β-CIT, lisuride), for the cholinergic system (e.g. epibatidine), for the glutaminergic system (e.g. mematine) or for the benzodiazepine system (e.g. flumazenil, iomazenil). Examples of metabolic active molecules that may be labeled are DOPA, Tyrosine, mIBG, MAO-I and analogues thereof.

Examples of cells that may be labeled are red and white blood cells.

As a result of the labeling of (biologically active) substrates with a compound of the general formula I, a further coordinated compound of the general formula $$\text{fac-}[M(CO)_3(X)_2(L_1)]^n \quad (II),$$

$$\text{fac-}[M(CO)_3(X)L_2]^n \quad (III) \text{ or}$$

$$\text{fac-}[M(CO)_3L_3]^n \quad (IV),$$

wherein:

M is Mn, $^{99m}$Tc, $^{186}$Re or $^{188}$Re;

L$_1$ is a monodentate ligand,

L$_2$ is selected from the group consisting of a bidenate ligand and two monodentate ligands, and L$_3$ is selected from the group consisting of a tridentate ligand, a monodentate ligand and a bidentate ligand, and three monodentate ligands;

X is H₂O or a halide ion;

n the sum of the charge of the ligands $L_1$ or $L_2$ or $L_3$ and X increased with one + charge is obtained.

After the labeling reaction the ligand X is usually H₂O. One of the H₂O ligands may, however, be replaced by a halide ion, when available, to neutralize the charge of the complex. This is often the case for compounds of the general formula III.

When the ligand $L_1$, $L_2$ or $L_3$ before and/or after labeling with the facial metal tricarbonyl compound is the biologically active molecule, the present invention gives easy access to compounds that directly can be used as a diagnostic and therapeutic agent.

Examples of monodentate ligands within the definition of $L_1$, $L_2$ and $L_3$ are (biologically active) substrates bearing groups such as phosphines, isonitriles, nitriles, imidazoles, thioethers and pyridine-like aromatic amines.

Examples of bidentate ligands within the definition of $L_2$ and $L_3$ are (biologically active) substrates bearing pyridine, imidazole or pyrazole groups, such as histidine, histamine, functionalized imidazole systems, bidentate thioethers, bidentate isocyanides, Schiff-base type ligands and picolinic acid.

Examples of tridentate ligands within the definition of $L_3$ are tris-pyrazolyl borate, tris-pyrazolylmethane, tris-imidazolyl borate, tris-pyrazolylmethane, 1,4,7-trithiacyclononane (9-aneS₃) and triazacyclononane (9-aneN₃), histidine, methionine, cysterine derivatized at the thiol group to give a thioether and cyclopentadienyl derivatives.

In some cases it may be advantageous to prepare the radiolabeled bioactive compound in one step. This objective can be achieved according to the present invention, with a method of preparing a compound of the general formula wherein:

M is Mn, $^{99m}$Tc, $^{186}$Re or $^{188}$Re;

$L_1$ is a monodentate ligand, $L_2$ is selected from the group consisting of a bidentate ligand and two monodentate ligands, and $L_3$ is selected from the group consisting of a tridentate ligand, a monodentate ligand and a bidentate ligand, and three monodentate ligands;

X is H₂O or a halide ion;

n the sum of the charge of the ligands $L_1$ or $L_2$ or $L_3$ and X increased with one + charge;

characterized in that a mixture of a base, ligands $L_1$ or $L_2$ or $L_3$, a reducing agent soluble in water but not substantially decomposed by water, and optionally a stabilizing agent is solved in a water containing solvent system containing a solution of the metal in the permanganate, pertechnetate or perrhenate form in the presence of carbon monoxide and optionally in the presence of halide.

Especially in the case of radiolabeled compounds it is frequently impossible to put the ready-for-use composition at the disposal of the user, in connection with the often poor shelf life of the radiolabeled compound and/or the short half-life of the radionuclide used. In such cases the user will carry out the labeling reaction with the metal in the clinical hospital or laboratory. For this purpose the various reaction ingredients are then offered to the user in the form of a so-called "kit". It will be obvious that the manipulations necessary to perform the desired reaction should be as simple as possible to enable the user to prepare from the kit the radioactive labeled composition by using the facilities that are at his disposal. Therefore the invention also relates to a kit for preparing a labeling composition, which labeling composition contains compound of formula I as the labeling agent.

Such a kit for the labeling of a biologically active substrate, according to the present invention, comprises (i) a reducing agent soluble in water but not substantially decomposed by water, (ii) a base, (iii) if desired, a stabilizing agent and/or a chelator and (iv) if desired one or more inert pharmaceutically acceptable carriers and/or formulating agents and/or adjuvants, at least one of said ingredients (i) to (iv) being stored in a container having an atmosphere containing a sufficient amount of carbon monoxide, said ingredients (i) to (iv) optionally independently being combined, and (v) instructions for use with a prescription for reacting the ingredients of the kit with a metal (M) selected from the group consisting of Mn, $^{99m}$Tc, $^{186}$Re or $^{188}$Re in the form of permetallate solution. Preferably, the kit comprises a lyophilized formulation in including a basic borate buffer and a reducing agent soluable in water but not substantially decomposed by water, the mixture being sealed in a container having a headspace comprising carbon monoxide, most preferably substantially pure carbon monoxide. In other embodiments, the kit can include a metal (M) as defined above. In still further embodiments, the kit can include a ligand ($L_3$), which preferably is a multidentate aminopolycarboxylate ligand.

It is the merit of the present invention, disclosing an easy way of preparing facial tricarbonyl metal compounds within a time-frame that is reasonable compared with the half-life time of the radioactive isotopes involved, and with high yields, that a kit can be prepared for the labeling of biologically active substrates with said facial tricarbonyl metal compounds.

In some cases it may be advantageous to enclose a bioactive substrate in the kit so that a kit is obtained for the preparation of a radiopharmaceutical composition.

Alternatively the biologically active compound is formed upon the reaction of the ligand with the facial metal tricarbonyl compound.

Such a kit for the preparation of a diagnostic and therapeutic pharmaceutical composition, according to a different embodiment of the present invention, comprises (i) a suitable substrate to be labeled with a metal selected from the group consisting of Mn, $^{99m}$Tc, $^{186}$Re or $^{188}$Re, (ii) a reducing agent soluble in water but not substantially decomposed by water, (iii) a base, (iv) if desired, a stabilizing agent and/or a chelator, (v) if desired one or more inert pharmaceutically acceptable carriers and/or formulating agents and/or adjuvants, at least one of said ingredients (i) to (v) being stored in a container having an atmosphere containing a sufficient amount of carbon monoxide, said ingredients (i) to (v) optionally independently being combined, and (vi)

instructions for use with a prescription for reacting the ingredients of the kit with said metal in the form of a permetallate solution.

The preparation of the diagnostic and therapeutic pharmaceutical composition with the aid of the above mentioned kit enclosing a (biologically active) substrate can take place in two alternative embodiments. In the first embodiment the facial tricarbonyl metal compound is prepared first and then reacted with the substrate to be labeled. In the second embodiment the reduction step is carried out in the presence of the substrate to be labeled, directly leading to the labeled compound.

The invention will now be described in greater detail with reference to the following specific Examples, which are offered by way of illustration and are not intended to limit the invention in any manner. Standard techniques well known in the art or the techniques specifically described below are utilized.

Example 1

Synthesis of $[^{99m}Tc(OH_2)_3(CO)_3]^+$

In a 10 mL closable vial the following chemicals are put together. 5.5 mg of $NaBH_4$, 4.0 mg $Na_2CO_3$ and 20.0 mg NaKtartrate. The vial is closed with a serum stopper and flushed for 10 minutes with carbon monoxide gas with the aid of a syringe. 3 mL of a 0.9% NaCl solution from a Mo-99/Tc-99m generator, having an activity of about 100 mCi, is added via the septum and the vial is heated to 75° C. during 30 minutes and then cooled to room temperature. The product is analyzed by TLC on standard Merck silica gel plates with methanol/concentrated HCl=99/1 as mobile phase followed by analysis of the silica gel plate by means of a radioactivity scanner. The yield of the reduction of pertechnetate to facial $[^{99m}Tc(OH_2)_3(CO)_3]^+$ is >95% according to TLC. After neutralizing the solution with a solution of PBS (phosphate buffer (pH=7.4, saline 0.9%) a neutral physiological solution, suitable for labeling is obtained.

Table 1 shows that solutions of $[^{99m}Tc(OH_2)_3(CO)_3]^+$ having an activity up to 700 mCi can be obtained under different reaction conditions.

Example 2

Preparation of Radiolabeled Peptides

Complexes of $[^{99m}Tc(CO)_3(n\text{-DTPA-}Y^3\text{-octreotate})]$, $[^{99m}Tc(CO)_3(iso\text{-DTPA-}Y^3\text{-octreotate})]$ and $[^{99m}Tc(CO)_3(DTPA'\text{-}Y^3\text{-octreotate})]$ were prepared as described below in this Example. Although the three complexes discussed herein each comprise an Octreotate peptide, complexes with other biomolecules such as proteins, sugars, etc., can be made in a similar fashion. These include but are not limited to those peptides as discussed in WO 98/48848, e.g., antibodies, His-neurotensin, and scFv. The synthesis of the Tc-99m tricarbonyl octreotates was based on the following two step procedure.

TABLE 1

Preparation of $[^{99m}Tc(OH_2)_3(CO)_3]^+$ Under Different Reaction Conditions

| Exp. | Stabilizing agent | Volume $TcO_4^-$ sol. (mL) | Activity (mCi) | Solvent | Temp. (° C.) | React. time (min.) | Yield (TLC) (%) |
|---|---|---|---|---|---|---|---|
| 1 | NaKtartrate | 3 | ≈100 | $H_2O$ | 75 | 30 | >95 |
| 2 | NaKtartrate | 3 | ≈400 | $H_2O$ | 75 | 30 | >95 |
| 3 | NaKtartrate | 3 | ≈700** | $H_2O$ | 75 | 30 | >95 |
| 4 | NaKtartrate | 3 | n.d.* | $H_2O$ | 75 | 30 | >95 |
| 5 | NaKtartrate | 6 | n.d.* | $H_2O$ | 75 | 30 | >95 |
| 6*** | NaKtartrate | 3 | n.d.* | $H_2O$ | 75 | 30 | 40 |
| 7 | — | 3 | n.d.* | $H_2O$ | 75 | 30 | 70 |
| 8 | Nacitrate | 3 | n.d.* | $H_2O$ | 75 | 30 | 20 |
| 9 | Naformate | 3 | n.d.* | $H_2O$ | 75 | 30 | 35 |
| 10 | NaKtartrate | 3 | n.d.* | $H_2O$/EtOH 80/20 | 75 | 30 | >95 |
| 11 | NaKtartrate | 3 | n.d.* | $H_2O$ | 100 | 10 | 60 |

*Activity not determined exactly, but always between 50 and 200 mCi.
**Activity determined after dilution to 1%.
***4.0 mg $Ca(OH)_2$ has been used as a base instead of 4.0 mg $Na_2CO_3$ Step 1: Preparation of $[^{99m}Tc(CO)_3(OH_2)_3]^+$ In the first step, $^{99m}TcO_4^-$ from a commercial generator (50–150 mCi, 1 mL) was added to a vial containing 2 mg of $NaBH_4$, 10 mg of NaKtartrate, and 2 mg of $Na_2CO_3$. The vial is stoppered and crimped, and the head space is then flushed for 5 minutes with carbon monoxide gas. The preparation was subsequently stirred and heated for 10 minutes at 100° C. to yield the $^{99m}Tc(I)$-tricarbonyl intermediate. Quality control effected by reverse phase HPLC (C-18 column with a 0.05 M TEAP (tetraethylammonium phosphate); pH=2.25/methanol gradient) showed >95% radiochemical purity (retention time=4.3 minutes).

Step 2: $[^{99m}Tc(CO)_3(DTPA'\text{-}Y^3\text{-Octreotate})]$

In the second step, 0.1 mL of the $[^{99m}Tc(CO)_3(OH_2)_3]^+$ intermediate, was added to a vial containing 1.0 mL of phosphate buffered saline (PBS). 50–125 µg of the peptide complex DTPA'-$Y^3$-Octreotate was then added, and the resulting solution was heated for 30 minutes at 75° C. Separation of the radiolabeled complex from radiochemical impurities was accomplished using a Waters C-18 Sep-Pak cartridge. The cartridge was first conditioned with ethanol followed by a water rinse. The reaction mixture was then applied to the top of the cartridge, washed with water to remove radiochemical impurities, and the product was subsequently eluted with ethanol. Quality control effected by reverse phase HPLC (C-18 column with a 0.05 M TEAP/methanol gradient) showed >95% radiochemical purity (retention times=20–21 minutes). [$^{99m}$Tc(CO)$_3$(iso-DTPA-Y$^3$-Octreotate)] and [$^{99m}$Tc(CO)$_3$(n-DTPA-Y$^3$-Octreotate)] were prepared exactly as was [$^{99m}$Tc(CO)$_3$(DTPA'-Y$^3$-Octreotate)] except that an iso-DTPA-Y$^3$-Octreotate or n-DTPA-Y$^3$-Octreotate peptide complex was used rather than the DTPA'-Y$^3$-Octreotate complex.

The synthetic data for the 3 radiolabeled Y$^3$-octreotates is given in Table 2.

TABLE 2

| Peptide | n-DTPA-Y$^3$-Octreotate | iso-DTPA-Y$^3$-Octreotate | DTPA = -Y$^3$-Octreotate |
|---|---|---|---|
| Amount of Peptide | 138 µg | 75 µg | 125 µg |
| Activity of Tc-99m | 9 mCi | 8 mCi | 9 mCi |
| HPLC Retention Time | 20.3 and 20.6 minutes (2 peaks) | 20.1 minutes | 19.8 minutes |
| Radiochemical Yield | 89% | 84% | 85% |
| Radiochemical Purity | 99% | 99% | 98% |

Example 3

Preparation of Radiolabeled Biological Substrates Using [$^{99m}$Tc(CO)$_3$(OH$_2$)$_3$]$^+$ and Aminopolycarboxylate Ligands It was found in studies presented herein in Example 5, that the DTPA'-Y$^3$-Octreotate has better biodistribution characteristics than do iso-DTPA-Y$^3$-Octreotate and n-DTPA-Y$^3$-Octreotate. Therefore additional studies have been performed with the DTPA'-Y$^3$-Octreotate. This Example discloses minor variations of the methods of Example 2 for preparing this compound. These methods are preferred over the methods of Example 2 and we have found them to be preferable to the methods disclosed in WO 98/48848.

Step 1: Preparation of [$^{99m}$Tc(CO)$_3$(OH$_2$)$_3$]$^+$

To a 10 mL sealed tubing vial containing the following lyophilized formulation: 20 mg lactose H$_2$O, 13 mg L-tartaric acid, 7.6 mg KBH$_4$, borate buffer at pH=11.6, and carbon monoxide in the headspace, is added 2 mL of $^{99m}$TcO$_4$$^-$ from a commercial generator (50–200 mCi). The vial is shaken vigorously for 30 seconds and placed in a boiling water bath for 15 minutes. Quality control effected by reverse phase HPLC (C-18 column with a 0.05 MTEAP; pH=2.25/methanol gradient) showed >90% radiochemical purity (retention time=4.3 minutes).

Step 2: [$^{99m}$Tc(CO)$_3$(DTPA'-Y$^3$-Octreotate)]

In the second step, 0.3 mL of the [$^{99m}$Tc(CO)$_3$(OH$_2$)$_3$]$^+$ intermediate, was added to a 2.0 mL vial followed by 35–40 µL of 1 N HCl. 100 µg of the peptide was added, and the resulting solution was heated for 35 minutes at 75° C. Separation of the radiolabeled complex from radiochemical impurities was accomplished using a Waters C-18 Sep-Pak cartridge. The cartridge was first conditioned with ethanol followed by a water rinse. The reaction mixture was then applied to the top of the cartridge, washed with water to remove radiochemical impurities, and the product was subsequently eluted with ethanol. Quality control effected by reverse phase HPLC (C-18 column with a 0.05 M TEAP/methanol gradient) showed >95% radiochemical purity (retention times=19–21 minutes). Specific Activity=250 Ci/mmol.

Example 4

Preparation of [$^{99m}$Tc(CO)$_3$(IDA-Glucose)

In addition to the Octreotate complexes discussed earlier, $^{99m}$Tc(CO)$_3$(IDA-glucose)] was synthesized for study. The preparation of [$^{99m}$Tc(CO)$_3$(OH$_2$)$_3$]$^+$ was synthesized as in Step 1 Example 3. Then for the second step, 0.3 mL of the [$^{99m}$Tc(CO)$_3$(OH$_2$)$_3$]$^+$ intermediate was added to a 2.0 mL vial followed by 35–40 µL of 1 N HCl. 1 mg of the glucose analog was added, and the resulting solution was heated for 60 minutes at 75° C. Separation of the radiolabeled complex from radiochemical impurities was accomplished using a Waters C-18 Sep-Pak cartridge. The cartridge was first conditioned with ethanol followed by water rinse. The reaction mixture was then applied to the top of the cartridge, washed with water to remove radiochemical impurities, and the product was subsequently eluted with ethanol. Quality control effected by reverse phase HPLC (C-18 column with a 0.05 M TEAP/methanol gradient) showed >95% radiochemical purity (retention times=16–17 minutes).

Example 5

Biodistribution of [$^{99m}$Tc(CO)$_3$(DTPA-Octreotates)] in CA20948 Tumored Lewis Rats These studies were performed to evaluate the biodistribution and imaging potential of these compounds in Lewis rats bearing CA20948 rat pancreatic tumor implants.

A) Methods

For each study, six (6) male Lewis rats bearing CA20948 tumor implants were anesthetized with Metofane gas and injected via the jugular vein with 200 µL (using the compounds of Example 2) or 50 µL (using the compound of Example 3) of test article containing ~50 µCi of activity. The animals were imaged for 100K counts under a gamma camera at 30 minute (n=3) and 4 hours (n=3) post injection after which time they were sacrificed and the following tissues removed for assay: blood, liver, kidneys, muscle, spleen, pancreas, small intestines, adrenals and tumor. The data are presented as % injected dose per gram and % injected dose per whole organ. The comparative data are also represented graphically.

B) Results

The soft tissues of the blood, liver and muscle indicated relatively low uptake. The somatostatin receptor expressing tissues of the pancreas, adrenals and tumor indicated significant and sustained uptake. The scintigraphs of the animals indicated sufficient uptake of the agent in the tumor. The amount of activity in the liver and GI tract with [$^{99m}$Tc(CO)$_3$(DTPA'-Y$^3$-Octreotate)] is significantly less compared to [$^{99mTc}$(CO)$_3$(His-Y$^3$-Octreotate)].

Figure 1A:
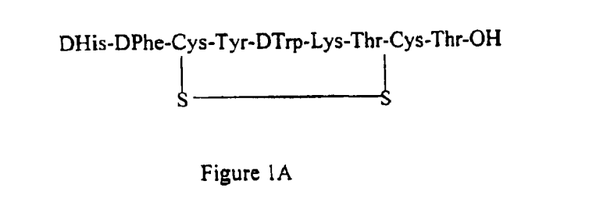
FIGS. 1A–E represent the structures of His-Tyr-3-Octreotate (FIG. 1A), n-DTPA-Tyr-3-Octreotate (FIG. 1B), iso-DTPA-Tyr-3-Octreotate (FIG. 1C), DTPA'-Tyr-3-Octreotate (FIG. 1D) and IDA-glucose (FIG. 1E).
Figure 1B:
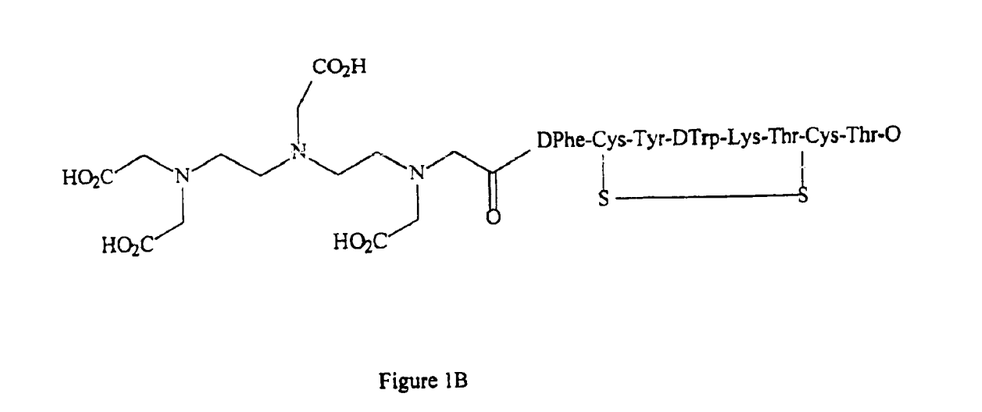
Figure 1C:
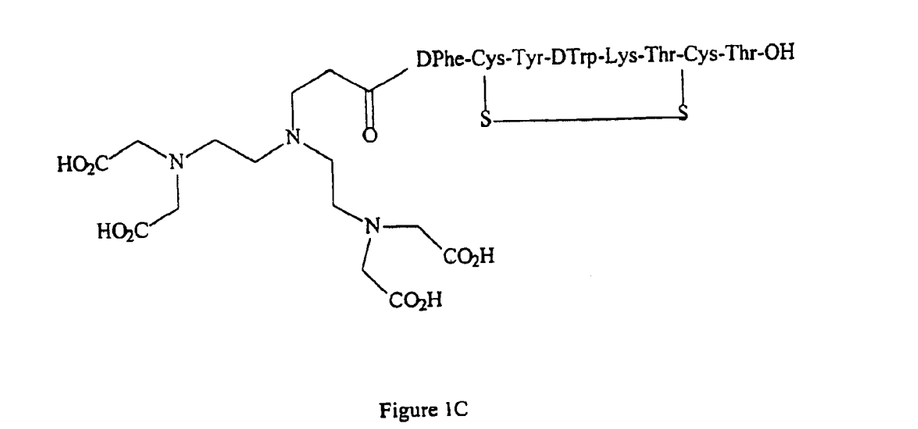
Figure 1D:
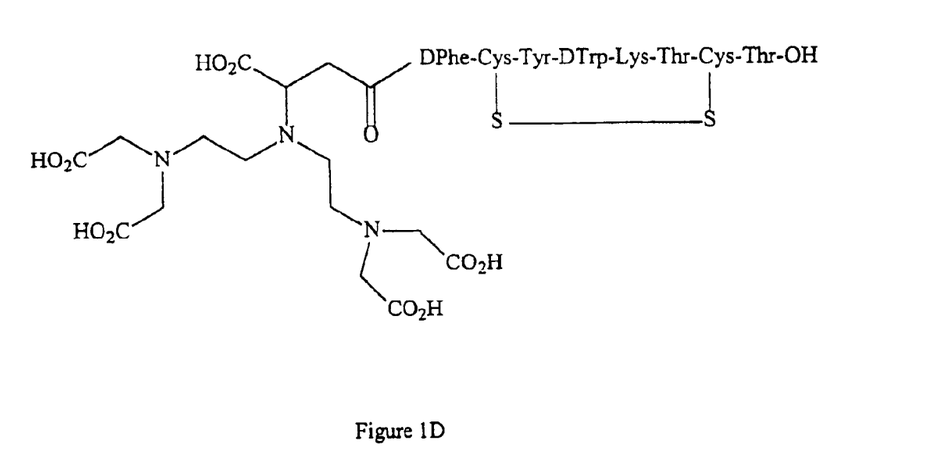
Figure 1E:
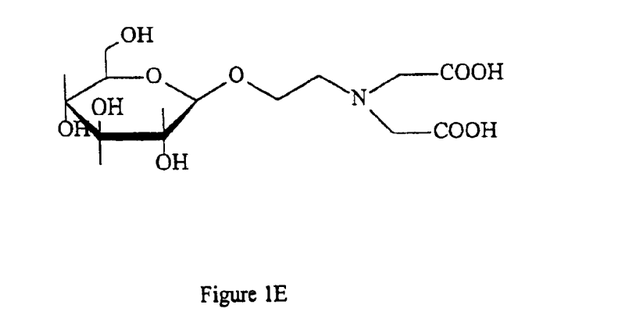
Figure 2:
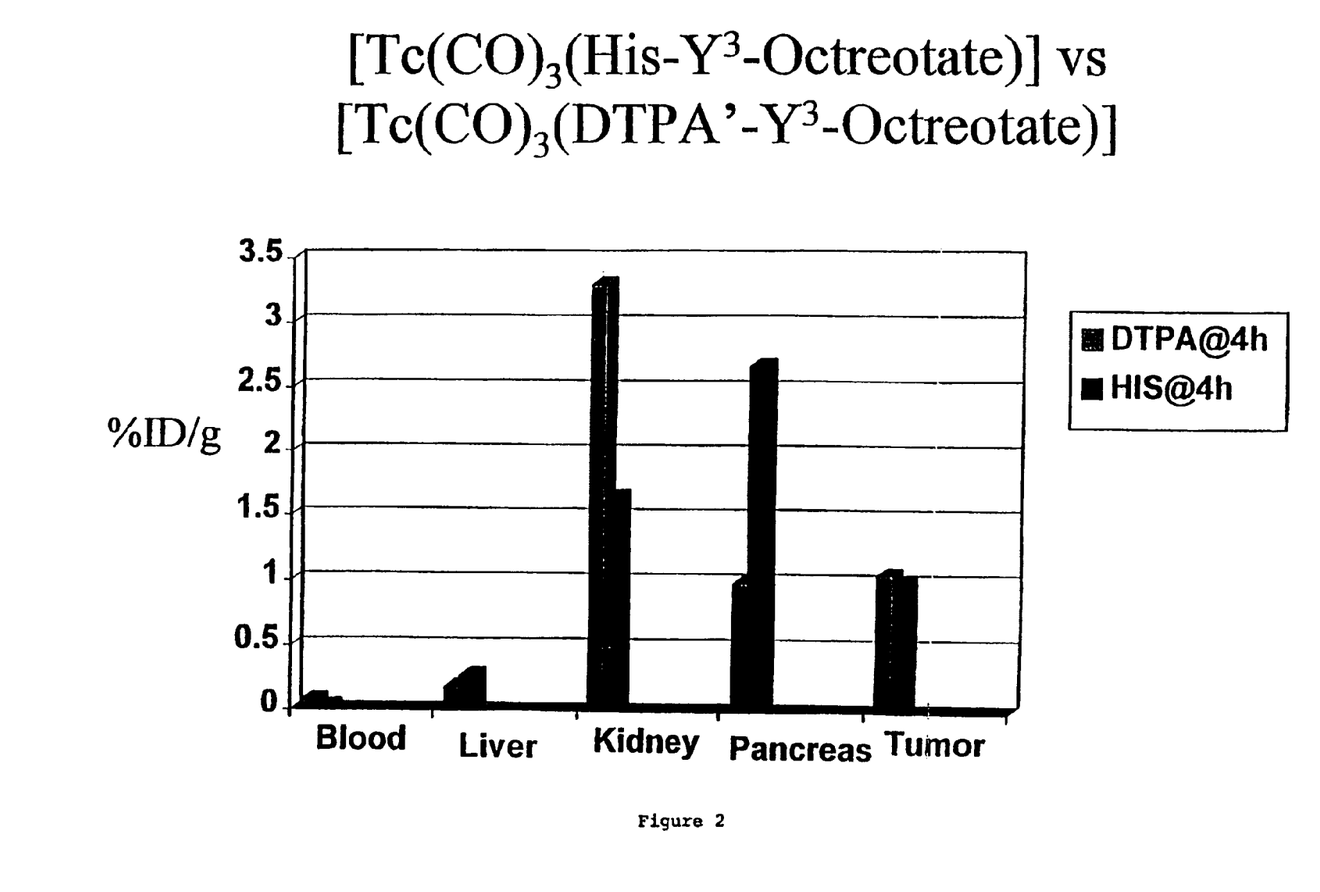
FIG. 2 is a graphic representation of the uptake of $[Tc(CO)_3(His-Y^3\text{-Octreotate})]$ and $[Tc(CO)_3(DTPA'-Y^3\text{-Octreotate})]$ in male Lewis rats bearing CA20948 tumor implants at 4 hours post injection. The scale shows the percent of the injected dose (ID) per gram of tissue as shown on the bottom of the graph.

The results of this study (Table 3 for the compounds of Example 2 and Table 4, FIG. 2 for the compounds of Example 3) indicate that these compounds did localize in the somatostatin receptor expressing tissues of the pancreas, adrenals and tumor with less hepatobiliary uptake and clearance with [$^{99m}$Tc(CO)$_3$(DTPA'-Y$^3$-Octreotate] compared to [$^{99m}$Tc(C))$_3$(His-Y$^3$-Octreotate)]. The peptides used are:

| Peptide | Radiolabeled Complex |
|---------|----------------------|
| MP-2423 | Tc-99m(CO)3-iso-DTPA-Tyr-3-Octreotate |
| MP-2138 | Tc-99m(CO)3-n-DTPA-Tyr-3-Octreotate |
| MP-2148 | Tc-99m(CO)3-DTPA'-Tyr-3-Octreotate |
| MP-2377 | Tc-99m(CO)3-His-Tyr-3-Octreotate |

Example 6

Urine Excretion and Metabolism for [$^{99m}$Tc(C)$_3$(DTPA'-Y$_3$-Octreotate)] vs. [$^{99m}$Tc(CO)$_3$(His-Y$^3$-Octreotate)]

During the general biodistribution studies, one additional animal per study was ligated to prevent urination prior to injection. The animal was kept anesthetized for 3 hours post injection, and was subsequently sacrificed, urine removed. The volume and activity of the urine was measured, and a sample was analyzed by HPLC using the method described above.

Both compounds remained essentially intact as determined by HPLC analysis. The % kidney clearance is about doubled for [$^{99m}$Tc(CO)$_3$(DTPA'-Y$^3$-Octreotate)] vs. [$^{99m}$Tc(CO)$_3$(His-Y$^3$-Octreotate)]. The results are shown in Table 5.

TABLE 3

| % ID/g ORGAN | (% ID) MP-2423 | (% ID) MP-2138 | (% ID) MP-2148 | (% ID) MP-2377 |
|---|---|---|---|---|
| | Time: 30 Minutes | | | |
| Blood | 0.472 ± 0.019 | 0.735 ± 0.027 | 0.471 ± 0.035 | 0.348 ± 0.013 |
| Tumor | 0.950 ± 0.012 | 0.847 ± 0.078 | 0.793 ± 0.041 | 1.274 ± 0.152 |
| Pancreas | 1.793 ± 0.039 | 1.556 ± 0.110 | 1.151 ± 0.032 | 2.672 ± 0.163 |
| Kidney | 2.231 ± 0.136 | 5.282 ± 0.014 | 2.141 ± 0.12 | 3.506 ± 0.438 |
| Liver | 0.327 ± 0.006 | 0.567 ± 0.015 | 0.494 ± 0.011 | 1.823 ± 0.098 |
| Tumor/Blood | 2 | 1.1 | 1.7 | 3.7 |
| Tumor/Liver | 3 | 1.3 | 1.6 | 0.7 |
| Tumor/Kidney | 0.4 | 0.14 | 0.37 | 0.4 |
| | Time: 4 hours | | | |
| Blood | 0.115 ± 0.001 | 0.218 ± 0.01 | 0.114 ± 0.005 | 0.03 ± 0.00 |
| Tumor | 0.848 ± 0.067 | 0.822 ± 0.13 | 0.769 ± 0.069 | 1.001 ± 0.066 |
| Pancreas | 2.025 ± 0.103 | 1.761 ± 0.089 | 0.956 ± 0.054 | 2.669 ± 0.114 |
| Kidney | 3.202 ± 0.111 | 5.703 ± 0.052 | 3.136 ± 0.08 | 1.638 ± 0.069 |
| Liver | 0.276 ± 0.004 | 0.516 ± 0.034 | 0.363 ± 0.022 | 0.283 ± 0.006 |
| Tumor/Blood | 7.4 | 3.7 | 6.7 | 33 |
| Tumor/Liver | 3 | 1.6 | 2.1 | 3.5 |
| Tumor/Kidney | 0.3 | 0.14 | 0.25 | 0.61 |

TABLE 4

| Organ (% ID/g at 4 hours p.i.) | [$^{99m}$Tc(CO)$_3$(DTPA'-Y$^3$-Octreotate)] | [$^{99m}$Tc(CO)$_3$(His-Y$^3$-Octreotate)] |
|---|---|---|
| Blood | 0.083 | 0.03 |
| Tumor | 1.06 | 1.00 |
| Pancreas | 0.99 | 2.67 |
| Liver | 0.19 | 0.28 |
| Kidney | 3.27 | 1.64 |

TABLE 5

| Compound | [$^{99m}$Tc(CO)$_3$(DTPA'-Y$^3$-Octreotate)] | [$^{99m}$Tc(CO)$_3$(His-Y$^3$-Octreotate)] |
|---|---|---|
| Activity/Volume of Urine | 10.4 μCi/1.5 mL | 5.8 μCi/1.5 mL |
| % ID | 30.7% | 15.2% |
| HPLC Analysis | 96% | 93% |

Example 7

Blocking Study of SST-2 Receptors in CA20948 Lewis Rats Using Cold Y$^3$-Octreotate to Determine Specificity for [$^{99m}$Tc(CO)$_3$(DTPA'-Y$^3$-Octreotate Two rats for each group were used. Group 1 received 500 μL PBS administered subcutaneously in the nape of the neck 30 minutes prior to the injection of [$^{99m}$Tc(CO)$_3$(DTPA'-Y$^3$-Octreotate)]. Group 2 received 350 μg Y$^3$-Octreotate in 500 μL phosphate buffered saline (PBS) administered subcutaneously in the nape of the neck 30 minutes prior to the injection of [$^{99m}$Tc(CO)$_3$(DTPA'-Y$^3$-Octreotate)].

Figure 3:
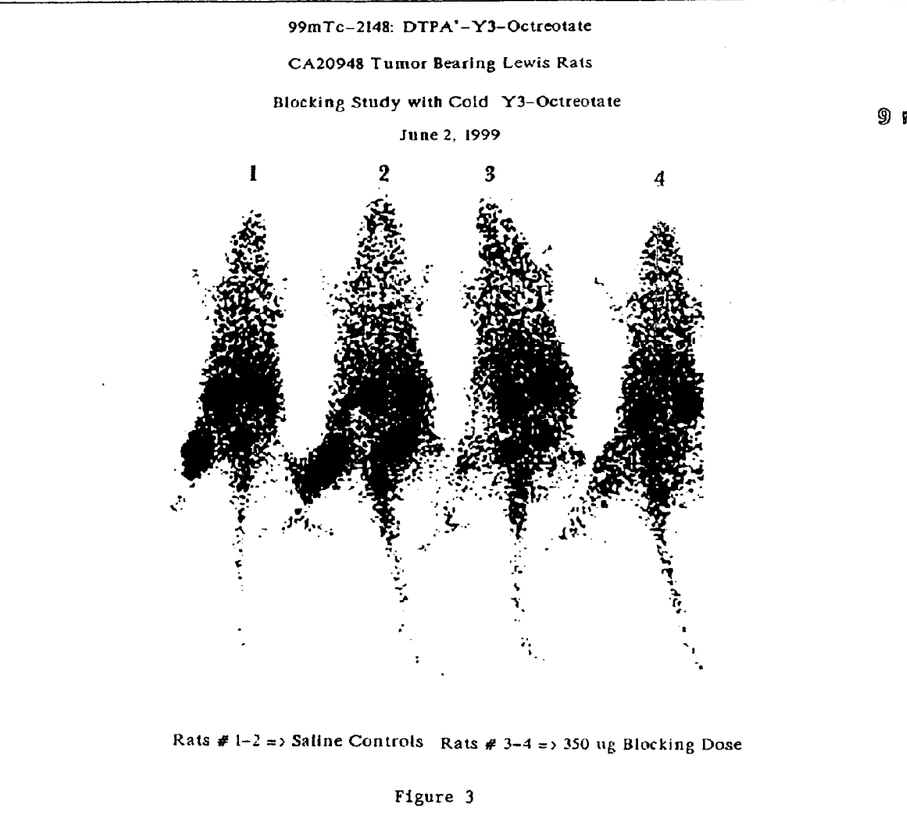
FIG. 3 is a scintigraph of rats which were injected with either cold peptide (rats 3 and 4) or a saline control (rats 1 and 2) and then 30 minutes later were injected with 50 $\mu$Ci of $[^{99m}Tc(CO)_3(DTPA'-Y^3\text{-Octreotate})]$. The scintigraph was taken 3 hours post injection.
Figure 4:
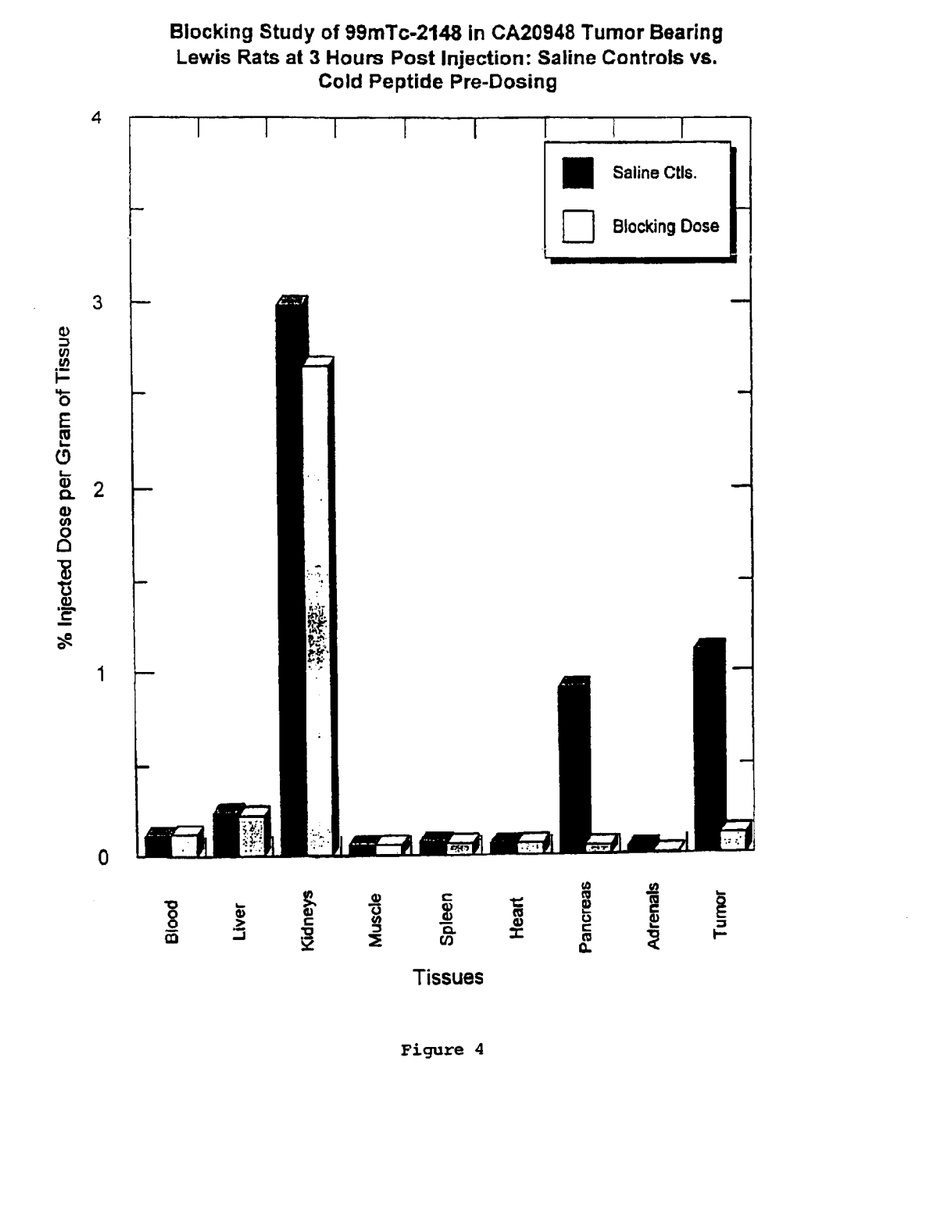
FIG. 4 is a graph comparing the uptake of 99mTc-2148 3 hours postinjection in various tissues of CA20948 tumor bearing Lewis rats for rats injected with saline or with a blocking dose of unlabeled peptide 30 minutes prior to injection of the labeled peptide.

30 minutes after injection of the cold peptide or saline control, the animals were anesthetized with Metofane gas and injected with 50 μL (50 μCi) of [$^{99m}$Tc(CO)$_3$(DTPA'-Y$^3$-Octreotate)]. At three hours post injection the animals were sacrificed, blood samples taken, and then the rats were scintigraphed for 100K counts (FIG. 3). At the conclusion of the scintigraphy, the animals were necropsied, and the following tissues removed for radioassay: liver, kidneys, muscle, spleen, heart, pancreas, adrenals, and tumor. The data were calculated as % injected dose per gram and % injected dose per whole organ. The data are shown in Table 6 and in FIG. 4.

In the somatostatin receptor-blocked animals, uptake in the somatostatin receptor expressing tissues was significantly reduced by 90% in the tumor, 95% in the pancreas, and 81% in the adrenals. Blood, liver, kidney, muscle, spleen, and heart did not change significantly between the two animal groups. These data indicate that [$^{99m}$Tc(CO)$_3$(DTPA'-Y$^3$-Octreotate)] is receptor specific.

TABLE 6

Biodistribution of 99mTC-2148 (DTPA'-Y3-Octreotate) in
CA20948 Tumor Bearing Lewis Rats at 3.0 Hours Post Injection

| | Rat #1 | | Rat #2 | | Average | |
|---|---|---|---|---|---|---|
| Tissue | % ID/g | % ID/organ | % ID/g | % ID/organ | % ID/g | % ID/organ |
| Blood | 0.122 | 1.330 | 0.107 | 1.552 | 0.115 | 1.441 |
| Liver | 0.268 | 2.313 | 0.204 | 2.389 | 0.236 | 2.351 |
| Kidneys | 3.324 | 6.229 | 2.646 | 7.414 | 2.985 | 6.822 |
| Muscle | 0.06 | 5.951 | 0.055 | 7.257 | 0.058 | 6.604 |
| Spleen | 0.081 | 0.040 | 0.062 | 0.048 | 0.072 | 0.044 |
| Heart | 0.068 | 0.046 | 0.056 | 0.051 | 0.062 | 0.049 |
| Pancreas | 1.216 | 0.787 | 0.616 | 0.736 | 0.916 | 0.762 |
| Adrenals | NA | 0.049 | NA | 0.035 | NA | 0.042 |
| Tumor | 1.354 | 5.343 | 0.857 | 5.022 | 1.115 | 5.183 |

| | Rat #3 | | Rat #4 | | Average | |
|---|---|---|---|---|---|---|
| Tissue | % ID/g | % ID/organ | % ID/g | % ID/organ | % ID/g | % ID/organ |
| Blood | 0.107 | 1.530 | 0.131 | 1.644 | 0.119 | 1.587 |
| Liver | 0.200 | 2.614 | 0.238 | 2.600 | 0.219 | 2.607 |
| Kidneys | 2.454 | 6.238 | 2.849 | 6.239 | 2.652 | 6.239 |
| Muscle | 0.053 | 6.897 | 0.061 | 6.967 | 0.057 | 6.932 |
| Spleen | 0.065 | 0.043 | 0.065 | 0.040 | 0.065 | 0.042 |
| Heart | 0.059 | 0.056 | 0.070 | 0.058 | 0.065 | 0.057 |
| Pancreas | 0.047 | 0.048 | 0.053 | 0.056 | 0.050 | 0.052 |
| Adrenals | NA | 0.007 | NA | 0.008 | NA | 0.008 |
| Tumor | 0.109 | 0.218 | 0.112 | 0.768 | 0.111 | 0.493 |

Rats 1 and 2 received saline
Rats 3 and 4 received 350 μg of cold peptide blocking dose While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Alberto R, et al. (1994a). *J. Nucl. Biol. Med.* 38:388–90.
Alberto R, et al. (1994b). A Low CO pressure synthesis of $(NEt)_2[MX_3(CO)_3]$ (M=Tc, Re) and its Substitution Behaviour in Water and Organic Solvents.≈ *Technetium in Chemistry and Nuclear Medicine,* No 4, Cortina International, Milano.
U.S. Pat. No. 4,232,000, Fawzi, issued Nov. 4, 1980.
U.S. Pat. No. 4,233,284, Fawzi, issued Nov. 11, 1980.
WO 98/48848
WO 96/30054

What is claimed is:

1. A method of preparing a compound of formula:

fac-[M(CO)₃L$_x$]$^n$  (II)

comprising reacting a ligand L$_x$ with a compound of formula (I)

fac-[M(CO)₃(OH₂)₃]⁺  (I)

wherein:

M is Mn, $^{99m}$Tc, $^{186}$Re or $^{188}$Re;

L$_x$ is a non-aromatic aminopolycarboxylate multidentate selected from the group consisting of diethylenetriamine-pentaacetic acid (DTPA), ethylenediaminetetraacetic acid (EDTA), 1,4,7,10-tetraazacyclododecane-1,4,7,10-tetraacetic acid (DOTA), nitrilotriacetic acid (NTA), and triazacyclononanetriacetate, said multidentate containing at least three carboxylate groups, and n is a charge of the ligand L$_x$ increased with one + charge.

2. The method of claim 1, wherein the reaction with ligand L$_x$ takes place in the presence of a halide.

3. The method of claim 1 wherein said method is performed between about 20° C. and 100° C.

4. The method of claim 1 wherein said method is performed at about 75° C.

5. The method of claim 1 wherein said ligand is not bidentate.

6. The method of claim 1 wherein said ligand is tridentate.

7. A compound of formula:

fac-[M(CO)₃L$_x$]$^n$  (II)

wherein:

M is Mn, $^{99m}$Tc, $^{186}$Re or $^{188}$Re;

L$_x$ is a non-aromatic multidentate aminopolycarboxylate ligand containing at least three carboxylate groups selected from the group consisting of diethylenetriamine-pentaacetic acid (DTPA), ethylenediaminetetraacetic acid (EDTA), 1,4,7,10-tetraazacyclododecane-1,4,7,10-tetraacetic acid (DOTA), nitrilotriacetic acid (NTA), and triazacyclononanetriacetate, said multidentate containing at least three carboxylate groups; and n is the sum of the charge of the ligands L$_x$.

8. The compound of claim 7, wherein $L_x$ is not a bidentate ligand.

9. A kit for carrying out the method of claim 1, comprising a lyophilized formulation including a basic borate buffer, a reducing agent soluble in water but not substantially decomposed by water and a metal M which is Mn, $^{99m}$Tc, $^{186}$Re or $^{188}$Re.

10. The kit of claim 9 wherein said reducing agent is $KBH_4$.

11. The kit of claim 9 wherein said formulation further includes lactose.

12. The kit of claim 9 wherein said formulation further includes L-tartaric acid.

13. The kit of claim 9 wherein $L_x$ is not a bidentate ligand.

* * * * *